United States Patent [19]

Pelster

[11] Patent Number: 5,981,806
[45] Date of Patent: Nov. 9, 1999

[54] PROCESS FOR THE PREPARATION OF HYDROXYNAPTHALENES

[75] Inventor: Thomas Pelster, Köln, Germany

[73] Assignee: Bayer Aktiengesellschaft, Leverkusen, Germany

[21] Appl. No.: 09/033,195

[22] Filed: Mar. 2, 1998

[30] Foreign Application Priority Data

Mar. 10, 1997 [DE] Germany .......................... 197 09 701

[51] Int. Cl.$^6$ .................................................. C07C 37/04
[52] U.S. Cl. .......................... 568/738; 568/735; 544/342
[58] Field of Search .................... 568/738, 735; 544/342

[56] References Cited

U.S. PATENT DOCUMENTS

| | | | |
|---|---|---|---|
| 3,555,117 | 1/1971 | Stahly et al. | 525/11 |
| 3,833,536 | 9/1974 | Steinbeck et al. | 524/90 |
| 4,158,670 | 6/1979 | Müller et al. | 558/57 |
| 5,350,853 | 9/1994 | Schmitt | 544/339 |

FOREIGN PATENT DOCUMENTS

| | | |
|---|---|---|
| 0 688 829 | 12/1995 | European Pat. Off. . |
| 3933932 | 4/1991 | Germany . |

Primary Examiner—Kathleen K. Fonda
Attorney, Agent, or Firm—Joseph C. Gil; Richard E. L. Henderson

[57] ABSTRACT

The present invention relates to a process for the preparation of hydroxynaphthalenes of formula (I)

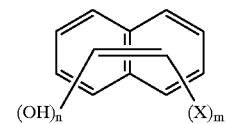

(I)

wherein n represents a number from 1 to 6,

X denotes $C_1$–$C_6$ alkyl, halogen, carboxyl, carboxylic acid ester, nitro, chlorosulphonyl, arylsulphonyl, hydroxyl, alkoxy, acyloxy, or an amino or aminosulphonyl that is unsubstituted or N-substituted with alkyl or aryl, or two radicals X, together with the adjacent carbon atoms to which they are bonded, form a fused-on aromatic, cycloaliphatic, or heterocyclic ring, and m denotes a number from 0 to 6, wherein if m is greater than 1, then each X can have different or identical meanings, by reacting (1) a naphthalenesulphonic acid of formula (II) or a salt thereof

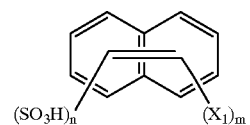

(II)

wherein n and m have the above meanings and $X_1$ has the same meaning as X or is $SO_3H$, with (2) alkali in the presence of (3) an alkylated urea derivative.

12 Claims, No Drawings

PROCESS FOR THE PREPARATION OF HYDROXYNAPTHALENES

PROCESS FOR THE PREPARATION OF HYDROXYNAPHTHALENES

The invention relates to a process for the preparation of hydroxynaphthalenes and to the use of these process products for bulk dyeing of plastics or as precursors, for example for the preparation of diisocyanates, pigments or dyestuffs.

Hydroxynaphthalenes, such as, for example, 8,8'-dihydroxynaphthazine, are described according to DE-A 21 48 850 for bulk dyeing of plastics. These compounds are prepared by the route disclosed in DE-A 39 33 932, starting from the corresponding disulphonic acid compound in the presence of a water-containing alcoholic-alkaline medium. A disadvantage of this process variant is, for example, a space-time yield which can still be improved. Furthermore, transfer to an industrial scale presents problems, since high-expenditure safety precautions would have to be taken because of the partial evolution of $H_2$ under the particular reaction conditions due to decomposition of the solvent used.

A process has now been found for the preparation of hydroxynaphthalenes of the formula (I)

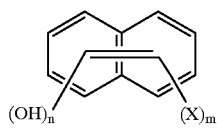

(I)

wherein
n represents a number from 1 to 6, preferably 1 or 2,
X denotes $C_1$–$C_6$-alkyl, halogen, carboxyl, carboxylic acid ester, nitro, chlorosulphonyl, arylsulphonyl, hydroxyl, alkoxy, acyloxy or an amino or aminosulphonyl which is optionally substituted by alkyl or aryl, or two radicals X, together with the adjacent C atom to which they are bonded, form a fused-on aromatic, cycloaliphatic or heterocyclic ring,
m denotes a number from 0 to 6, where, if
m is greater than 1,
X can in each case have meanings which are different from, or identical to, those mentioned above,
characterized in that naphthalenesulphonic acids of the formula (II) or salts thereof, preferably alkali metal salts thereof, such as Na or K salts,

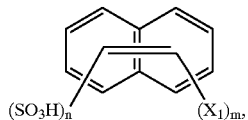

(II)

wherein n and m have the abovementioned meanings and
$X_1$ has the same meaning as X, but $SO_3H$ substituents optionally replace OH substituents bonded to aromatic radicals,
are reacted with alkali in the presence of an alkylated urea derivative.

The optional other meaning of $X_1$ in relation to X takes into account that not only the sulpho groups of the naphthalene nucleus but also those on other aromatic radicals of the starting substance are converted into OH substituents.

The process according to the invention is particularly suitable for the preparation of compounds of the formula (I) wherein
m represents a number from 2 to 6, in particular 2 or 3, and two radicals
X together denote a radical of the formula (a)

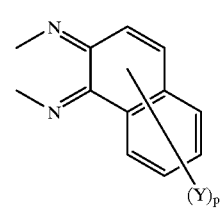

(a)

or (b)

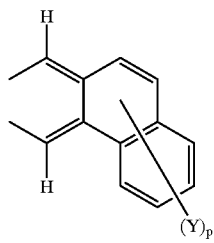

(b)

which is linked to two adjacent C atoms of the naphthalene ring,
wherein
Y denotes $C_1$–$C_6$-alkyl, halogen, in particular Cl, COOH, carboxylic acid ester, in particular $C_1$–$C_4$-alkyl ester, nitro, chlorosulphonyl, arylsulphonyl, hydroxyl, alkoxy, acyloxy or an amino or aminosulphonyl which is optionally substituted by alkyl or aryl,
p denotes a number from 0 to 6, where, if
p is greater than 1,
Y can in each case have meanings which are different from, or identical to, those mentioned above.

Compounds of the formula I wherein two radicals $X_1$ together represent a radical of the formula (a) are designated as compounds of the formula (Ia) below. Compounds of the formula I wherein two radicals X together denote a radical of the formula (b) are designated as compounds (Ib) below.

In a particular embodiment, the radical a) or b) is bonded to the 1,2-position of the naphthalene ring.

Particularly preferred compounds of the formula (I) are those which correspond to the formula (Ic)

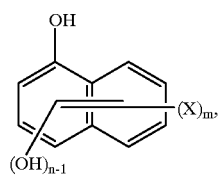

(Ic)

wherein
n represents 1 or 2 and X and m have the abovementioned meanings.

In the context of this Application, and unless described otherwise, alkyl preferably represents $C_1$–$C_4$-alkyl, aryl preferably represents phenyl and alkoxy preferably represents $C_1$–$C_4$-alkoxy, where these radicals are optionally substituted.

These are, in particular, the compounds mentioned below

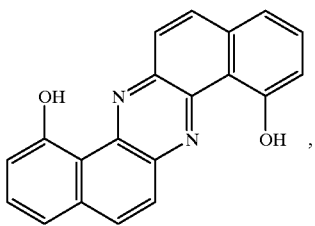
(Id)

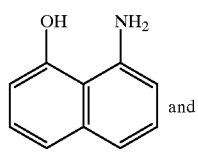
(Ie)

and

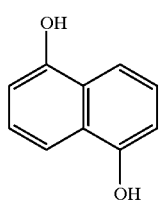
(If)

Possible alkylated urea derivatives are, for example, open-chain derivatives, such as dialkylureas, in particular di-$C_1$–$C_4$-alkylureas, such as dimethylurea, or tetraalkylureas, in particular tetra-$C_1$–$C_4$-alkylureas, such as trimethylurea, or cyclic urea derivatives, such as N,N'-dialkylalkyleneureas, in particular N,N'-di-$C_1$–$C_4$-alkyl-$C_2$–$C_4$-alkyleneureas, particularly preferably N,N'-dimethylethyleneurea of the formula

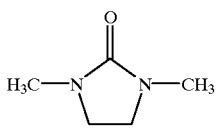

and N,N'-dimethylpropyleneurea of the formula

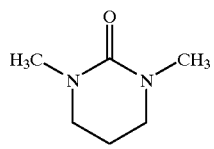

or N,N',N''-trialkylthexahydro-1,3,6-triazin-2-ones, such as 1,3,6-trimethylhexahydro-1,3,6-triazin-2-one of the formula

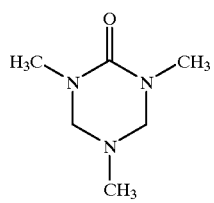

Such cyclic urea derivatives are known, for example, from EP-A 688 829 and from DE-A 42 17 954.

The alkylated urea derivative or mixture of alkylated urea derivatives is/are preferably employed in an amount of 0.005 to 10 parts by weight, preferably 0.1 to 5 parts by weight, particularly preferably 1 to 3 parts by weight per part by weight of the naphthalenesulphonic acid compound of the formula (II).

If appropriate, the alkylated urea derivative is employed in a mixture with an inert organic solvent, such as dimethylsulphoxide (DMSO), pyridine, toluene, xylene or nitrobenzene.

In the context of this Application, alkali is understood as meaning both the hydroxides of the alkali metals and those of the alkaline earth metals. Suitable alkalis are alkali metal hydroxides, in particular NaOH or KOH, and $Ca(OH)_2$. Preferably, 1 to 3 parts by weight, in particular 1 to 2 parts by weight, of alkali are employed per part by weight of the naphthalenesulphonic acid of the formula (II).

The process according to the invention can also be carried out in the presence of water, preferably not more than 10% by weight, based on the reaction medium, of water being employed. As a rule, reaction medium is to be understood as meaning all the constituents apart from the compounds of the formulae (I) and (II) and the alkali. In a preferred embodiment, the reaction medium comprises 40 to 100% of the alkylated urea derivative, 0 to 10% of water and 0 to 10% of an inert organic solvent, the sum of all the constituents giving 100%.

In general, the process according to the invention is carried out at a temperature of at least 120° C., preferably at 150 to 180° C.

If the reaction medium comprises water or other compounds which boil below the reaction temperature, the reaction is preferably carried out under pressure. The process according to the invention is then carried out, for example, in an autoclave, a pressure of 1 to 5 bar being preferred.

When the reaction has ended, which can be monitored by chromatography, the reaction mixture is preferably cooled to a temperature of 50–70° C. and diluted with an alcohol, for example methanol, with pyridine or pyridine-water mixtures or directly with water, and the reaction product is isolated in the customary manner by filtering off and washing.

The invention also relates to a process for bulk dyeing of plastics using the dyestuffs obtained by the process according to the invention, preferably those of the formula Ia or Ib, and to the plastics dyed with these.

Bulk dyeing here is to be understood as meaning, in particular, processes in which the dyestuff is incorporated into the molten composition of the plastic, for example with the aid of an extruder, or in which the dyestuff is already added to starting components for the preparation of the plastic, for example monomers before the polymerization.

Particularly preferred plastics are thermoplastics, for example vinyl polymers, polyesters and polyamides.

Suitable vinyl polymers are polystyrene, styrene/acrylonitrile copolymers, styrene/butadiene copolymers, styrene/butadiene/acrylonitrile terpolymers, polymethacrylate and the like.

Polyesters which are furthermore suitable are: polyethylene terephthalates, polycarbonates and cellulose esters.

Polystyrene, styrene copolymers, polycarbonates and polymethacrylate are preferred. Polystyrene is particularly preferred.

The high molecular weight compounds mentioned can be present individually or in mixtures, as plastic compositions or melts.

The dyestuffs of the formula Ia or Ib obtained according to the invention are preferably used in finely divided form, it being possible, but not necessary, to co-use dispersing agents.

If the dyestuffs Ia or Ib are employed after the polymerization, they are mixed or ground with the granules of plastic in the dry state and this mixture is plasticized and homogenized, for example on mixing rolls or in screws. However, it is also possible to add the dyestuffs to the molten composition and to distribute them homogeneously by stirring. The material predyed in this way is then further processed in the customary manner, for example by spinning to bristles, filaments and the like, or by extrusion or the injection moulding process to give mouldings.

Since the dyestuffs of the formula Ia or Ib are resistant to polymerization catalysts, in particular peroxides, it is also possible to add the dyestuffs to the monomeric starting materials and then to carry out the polymerization in the presence of polymerization catalysts. For this, the dyestuffs are preferably dissolved in the monomeric components or mixed intimately with them.

The dyestuffs of the formula Ia or Ib are preferably employed for dyeing the polymers mentioned in amounts of 0.0001 to 1% by weight, in particular 0.01 to 0.5% by weight, based on the amount of polymer.

Corresponding valuable opaque dyeings can be obtained by addition of pigments which are insoluble in the polymers, such as, for example, titanium dioxide.

Titanium dioxide can be used in an amount of 0.01 to 10% by weight, preferably 0.1 to 5% by weight, based on the amount of polymer.

Transparent or opaque brilliant dyeings of good heat resistance and good fastness to light and weather are obtained by the process according to the invention.

Mixtures of various dyestuffs, preferably dyestuffs of the formula Ia and/or Ib, and/or mixtures of dyestuffs of the formula Ia or Ib with other dyestuffs and/or inorganic or organic pigments can also be employed in the dyeing process according to the invention.

The invention furthermore relates to the use of the compounds of the formula (I) obtained by the process according to the invention, in particular those of the formula Ic, as precursors for the preparation of isocyanates and pigments.

In this case, isocyanates are prepared, for example, by reaction of dihydroxynaphthalene of the formula (If) with ammonia/bisulphite (Bucherer reaction) and then with phosgene.

Dyestuffs, for example azo dyestuffs, are prepared in this case, for example, by diazotization of an aromatic amine and coupling to compounds of the formula I. 2-Aminophenol-4-sulphonic acid, for example, may be mentioned as an aromatic amine and the dihydroxynaphthalene of the formula (If) may be mentioned as a compound of the formula I.

EXAMPLES

Example 1

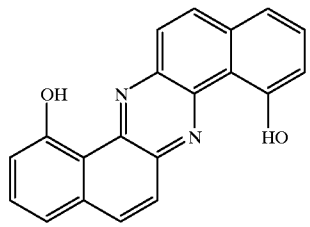

A mixture of 100 g of N,N'-dimethylethyleneurea and 60 g of potassium hydroxide was heated to 130° C. 22 g (0.5 mol) of 8,8'-naphthazinedisulphonic acid were introduced into this mixture under a nitrogen atmosphere in the course of 30 minutes. The reaction mixture was heated at 160° C. for 18 hours until the starting substance was no longer detectable by chromatography. It was then cooled to 80° C., 400 ml of water were added and the product was filtered off, washed neutral with water and dried. 14 g (92% of theory) of 8,8'-dihydroxynaphthazine, which dyes plastics in clear yellow shades in this form, were obtained.

Example 2

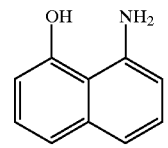

A mixture of 100 g of N,N'-dimethylpropyleneurea and 60 g of potassium hydroxide was heated to 150° C. 22 g of 1-amino-naphthazine-8-sulphonic acid were introduced into this mixture under a nitrogen atmosphere in the course of 30 minutes. The reaction mixture was heated at 160° C. for 12 hours until the starting substance was no longer detectable by chromatography. It was then cooled to 80° C., 400 ml of water were added, the mixture was neutralized with hydrochloric acid and the product was filtered off, washed with water and dried. 12 g (75% of theory) of 1-amino-8-hydroxynaphthalene were obtained.

Example 3

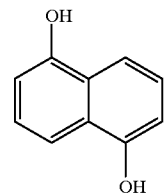

A mixture of 100 g of N,N'-dimethylpropyleneurea and 60 g of potassium hydroxide was heated to 150° C. 29 g (0.1 mol) of 1,5-naphthalenedisulphonic acid were introduced into this mixture under a nitrogen atmosphere in the course of 30 minutes. The reaction mixture was heated at 160° C. for 22 hours until the starting substance was no longer detectable by chromatography. It was then cooled to 80° C., 400 ml of water were added, the mixture was neutralized with hydrochloric acid and the product was filtered off, washed with water and dried. 14 g (87% of theory) of 1,8-dihydroxynaphthalene, which can be used in the present form as a dyestuff intermediate product and for the preparation of isocyanates, were obtained.

I claim:

1. A process for the preparation of hydroxynaphthalenes of formula (I)

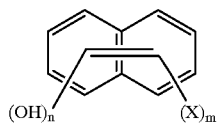

wherein
n represents a number from 1 to 6,
X denotes $C_1$–$C_6$ alkyl, halogen, carboxyl, carboxylic acid ester, nitro, chlorosulphonyl, arylsulphonyl, hydroxyl, alkoxy, acyloxy, or an amino or aminosulphonyl that is unsubstituted or N-substituted with alkyl or aryl, or two radicals X, together with the adjacent carbon atoms to which they are bonded, form a fused-on aromatic, cycloaliphatic, or heterocyclic ring, and
m denotes a number from 0 to 6, with the proviso that if m is greater than 1, then each X can have different or identical meanings, comprising reacting (1) a naphthalenesulphonic acid of formula (II) or a salt thereof

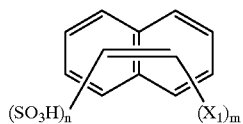

wherein
n and m have the above meanings and
$X_1$ has the same meaning as X or is $SO_3H$,
with
(2) alkali in the presence of
(3) an alkylated urea derivative.

2. The process according to claim 1, wherein the reaction is carried out at a temperature of at least 120° C.

3. The process according to claim 1, wherein n represents 1 or 2.

4. The process according to claim 1, wherein
m represents a number from 2 to 6, and
two radicals X, together with the adjacent carbon atoms of the naphthalene ring, denote

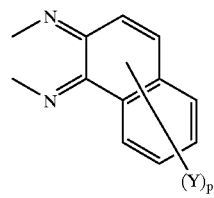

Mo-4780 wherein
Y denotes $C_1$–$C_6$ alkyl, halogen, COOH, carboxylic acid ester, nitro, chlorosulphonyl, arylsulphonyl, hydroxyl, alkoxy, acyloxy, or an amino or aminosulphonyl that is unsubstituted or N-substituted with alkyl or aryl,
p denotes a number from 0 to 6, with the proviso that if p is greater than 1, then each Y can have different or identical meanings.

5. The process according to claim 4, wherein m represents 2 or 3.

6. The process according to claim 4, wherein Y denotes Cl.

7. The process according to claim 1, wherein the hydroxynaphthalene prepared by said process is a compound of formula (Ic)

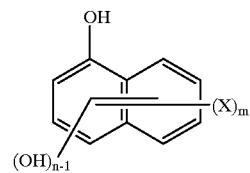

wherein
n represents 1 or 2,
X denotes $C_1$–$C_6$ alkyl, halogen, carboxyl, carboxylic acid ester, nitro, chlorosulphonyl, arylsulphonyl, hydroxyl, alkoxy, acyloxy, or an amino or aminosulphonyl that is unsubstituted or N-substituted with alkyl or aryl, or two radicals X, together with the adjacent carbon atoms to which they are bonded, form a fused-on aromatic, cycloaliphatic, or heterocyclic ring, and
m denotes a number from 0 to 6, with the proviso that if m is greater than 1, then each X can have different or identical meanings.

8. The process according to claim 1, wherein the hydroxynaphthalene prepared by said process is

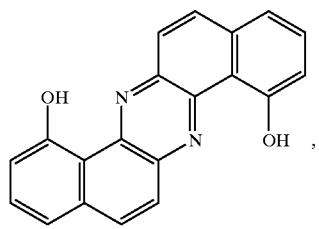

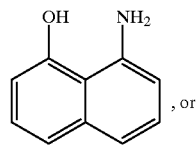

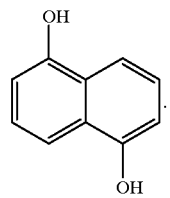

9. The process according to claim 1, wherein the alkylated urea derivative is an open-chain or cyclic urea derivative.

10. The process according to claim 1, wherein the alkylated urea derivative is a dialkylurea, a tetraalkylurea, an N,N'-dialkylalkyleneurea, or an N N',N"-trialkylhexahydro-1,3,6-triazin-2-one.

11. The process according to claim 1, wherein the alkylated urea derivative is (i) N,N'-dimethylethyleneurea of the formula
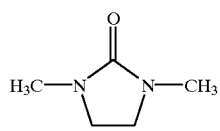
(ii) N,N'-dimethylpropyleneurea of the formula
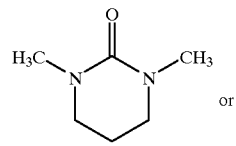 or
(iii) 1,3,6-trimethylhexahydro-1,3,6-triazin-2-one of the formula
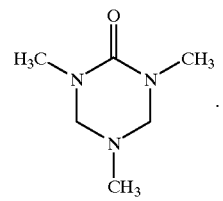
12. The process according to claim 1, wherein the alkylated urea derivative is dimethylurea or tetramethylurea.